US012746412B2

(12) United States Patent
Voet et al.

(10) Patent No.: US 12,746,412 B2
(45) Date of Patent: Sep. 29, 2026

(54) METHOD AND SYSTEM FOR TREATMENT PLANNING

(71) Applicant: Elekta, Inc., Atlanta, GA (US)

(72) Inventors: Peter Voet, Atlanta, GA (US); Chunhua Men, Atlanta, GA (US); Spencer Marshall, Brandon, FL (US)

(73) Assignee: Elekta, Inc., Atlanta, GA (US)

(*) Notice: Subject to any disclaimer, the term of this patent is extended or adjusted under 35 U.S.C. 154(b) by 716 days.

(21) Appl. No.: 18/315,955

(22) Filed: May 11, 2023

(65) Prior Publication Data

US 2024/0374924 A1 Nov. 14, 2024

(51) Int. Cl.
*A61N 5/10* (2006.01)
*G16H 20/40* (2018.01)

(52) U.S. Cl.
CPC ........... *A61N 5/1031* (2013.01); *G16H 20/40* (2018.01)

(58) Field of Classification Search
CPC ............................ A61N 5/1013; G16H 20/40
See application file for complete search history.

(56) References Cited

U.S. PATENT DOCUMENTS 6,064,203 A 5/2000 Bottomley
6,963,771 B2 11/2005 Scarantino et al.
7,317,192 B2 1/2008 Ma
8,492,735 B2 7/2013 Brand
9,884,206 B2 2/2018 Schulte et al.
10,737,114 B2 8/2020 Gattiker et al.
10,835,760 B2 11/2020 Kuusela et al.
2005/0111621 A1* 5/2005 Riker .................... G16H 20/40 378/65
2012/0123184 A1 5/2012 Otto et al.
2015/0202464 A1 7/2015 Brand et al.
2016/0008630 A1 1/2016 Ranganathan et al.
(Continued)

FOREIGN PATENT DOCUMENTS

CN 115463352 12/2022
EP 3681600 7/2020
WO 2017178257 10/2017

OTHER PUBLICATIONS

ELEKTA AB, "", Monaco Training Guide, Document ID: LTGMON0530, (2017), 1313 pgs.
(Continued)

*Primary Examiner* — Hugh Maupin
(74) *Attorney, Agent, or Firm* — Schwegman Lundberg & Woessner, P.A.

(57) ABSTRACT

A computer-implemented method may be provided to aid in radiation treatment planning, the method comprising: receiving a reference objective, the reference objective representing a goal to be achieved by a radiotherapy system; selecting a cost function associated with the reference objective from a plurality of cost functions, the selected cost function being associated with an assigned initial weight value, the assigned initial weight value corresponding to sensitivity of an example dose distribution relative to changes in the selected cost function; applying an optimization procedure to a radiation treatment plan for radiation treatment in a patient according to the received reference objective, wherein the optimization procedure uses the assigned initial weight value of the selected cost function and seeks to minimize the selected cost function.

16 Claims, 8 Drawing Sheets

(56) References Cited

U.S. PATENT DOCUMENTS

| | | | | |
|---|---|---|---|---|
| 2016/0082287 | A1* | 3/2016 | Isola .................... | A61N 5/1047 600/1 |
| 2017/0246477 | A1 | 8/2017 | Zhang et al. | |
| 2018/0304099 | A1 | 10/2018 | Li et al. | |
| 2021/0138267 | A1 | 5/2021 | Nord et al. | |
| 2021/0316157 | A1 | 10/2021 | Lynch et al. | |

OTHER PUBLICATIONS

"European Application No. 24175411.8, Extended European Search Report dated Sep. 16, 2024", (Sep. 16, 2024), 7 pgs.

* cited by examiner

METHOD AND SYSTEM FOR TREATMENT PLANNING

TECHNICAL FIELD

The present disclosure relates to methods and systems for treatment planning. More specifically, the present disclosure relates to a computer-implemented method for radiation treatment planning, and data processing apparatuses, computer programs, and non-transitory computer-readable storage mediums configured to execute methods for radiation treatment planning.

BACKGROUND

Radiation therapy or radiotherapy may be described as the use of ionising radiation to damage or destroy unhealthy cells in both humans and animals. The ionising radiation may be directed to tumours on the surface of the skin or deep inside the body. Common forms of ionising radiation include X-rays and charged particles. An example of a radiotherapy technique is Gamma Knife®. where a patient is irradiated using a number of lower-intensity gamma rays that converge with higher intensity and high precision at a targeted region (e.g., a tumour). Another example of radiotherapy comprises using a linear accelerator ("linac"), whereby a targeted region is irradiated by high-energy particles (e.g., electrons, high-energy photons, and the like). In another example, radiotherapy may be provided using a heavy charged particle accelerator (e.g., protons, carbon ions, and the like).

The placement and dose of the radiation beam may be accurately controlled to provide a prescribed dose of radiation to the target region (e.g., the tumour) and to reduce damage to surrounding healthy tissue (known as organs at risk or OARs). An aspect of treatment planning concerns determining suitable characteristics of radiation to be delivered to produce a safe and effective dose. Characteristics of radiation relate to, for example, a fluence pattern or distribution. The fluence pattern may be dependent on beam arrangements, energies, and field sizes, which are in turn related to controllable parameters (which are optimizable). By determining suitable values for those parameters, a suitable fluence pattern may be obtained. A treatment plan may be determined by a treatment planning system.

A radiation therapy treatment plan (treatment plan, or simply plan) may be established using an optimization procedure to determine a set of optimum parameter values or optimum variable values that are expected to deliver a suitable dose. The optimization procedure may be based on clinical and dosimetric objectives and constraints. Examples of clinical and dosimetric objectives and constraints include maximum, minimum, and mean doses to target regions and surrounding regions (e.g., tumours and critical organs). Clinical and dosimetric objectives and constraints may be referred to as treatment planning objectives. Optimization is usually carried out with respect to one or more treatment plan parameters to reduce beam-on time, improve dose uniformity, etc.

A treatment planning procedure may include using an image (two- or three-dimensional) of the patient to identify a target region and to identify critical organs near the target region. The target region (or area to be treated, e.g., a planned target volume, PTV), and surrounding region (or Organs at Risk, OARs) may be identified using segmentation. After segmentation, a dose plan may be created for the patient indicating the desirable amount of radiation to be received by the target region and/or the surrounding region.

The target region may have an irregular volume and may be distinctive in terms of its size, shape, and position.

In a practical example, multiple anatomical structures (target regions and/or surrounding regions) may be present. For example, in a head and neck treatment, there may be over 20 anatomical structures. For each structure, compliance with various treatment-planning objectives may be desired. Structures and their objectives may be assigned different priorities in order to achieve a clinically acceptable plan. Determining a treatment plan to meet the various objectives is time-consuming and complex.

Creation of a radiation treatment plan is typically a time-consuming process where a planner may try to comply with various treatment objectives or constraints—considering their individual importance—to produce a radiation treatment plan that is clinically acceptable. Common issues faced when creating radiation treatment plans that involve optimization procedures include lengthy optimization times and high computational burdens required to achieve safe and satisfactory results. These processes often involve trial-and-error on the part of the user (e.g., a treatment planner, dosimetrist, clinician, or health care worker), may be time-consuming, and are further complicated with the addition of further objectives and constraints.

Therefore, it is desirable to reduce the planning time with an improved radiotherapy treatment planning workflow.

SUMMARY

According to an aspect, there is provided a computer-implemented method for radiation treatment planning. The method comprises receiving a reference objective, the reference objective representing a goal to be achieved by a radiotherapy system. In this sense, the reference objective may be an anatomy-specific function that establishes the dose and/or biological response goal. Such a reference objective may not be necessarily met in an optimization procedure—instead, the reference objective is a goal that the optimization procedure tries to achieve. For instance, the reference objective may be a dose-based reference objective, which establishes a goal of a maximum absorbed dose (provided in SI units of gray (Gy)) for a target region of a patient. A reference objective may be a biological-based reference objective, which takes into account the notion that higher doses may be tolerated by a particular biological structure or tissue when the irradiated volume is reduced. The reference objective may be an objective for a target region (i.e., the target for radiation treatment, e.g., a tumour) or may be an objective for a surrounding region (i.e., a region or regions surrounding the target region). The surrounding region (or neighbouring region, or OAR) need not be in physical contact with the target region, rather the surrounding region may include regions of the patient other than the target region in which the user wishes to limit or otherwise control the absorbed dose.

The method further comprises selecting a cost function associated with the reference objective from a plurality of cost functions. The selected cost function is associated with an assigned initial weight value. That is, each cost function of the plurality of cost functions may be mapped to an assigned initial weight value. For example, a first cost function may be associated with a first assigned initial weight value, a second cost function may be associated with a second assigned initial weight value, and so on; of course, the first assigned initial weight value and the second assigned initial weight value may be the same value. The assigned initial weight value corresponds or maps to the sensitivity of an example or reference dose distribution relative to changes in the selected cost function (or output thereof). Equally, the assigned initial weight value corresponds or maps the sensitivity of the selected cost function (or output thereof) to changes in the example dose distribution. That is, the assigned initial weight value may be used to indicate the scale of change in a dose distribution (e.g., a dose map or dose distribution, indicating spatial distribution of intensity of radiation dose) given a change in the output of the selected cost function.

The method further comprises applying an optimization procedure to a radiation treatment plan for radiation treatment in a patient according to the received reference objective. The optimization procedure uses the assigned initial weight value of the selected cost function. For example, the optimization procedure scales the cost function value (the output of the cost function) by the assigned initial weight value. The optimization procedure seeks to minimize the selected cost function (or output thereof). In this way, the optimization procedure seeks to determine treatment parameters (or values thereof) that are expected to result in a treatment plan that achieves the reference objective (or goal represented by the reference objective) as closely as practicable (that is, in respect of processing and/or time constraints).

As an example, a 1% change in the integrated intensity of an example dose map may be associated with a 5% change in a first cost function value (relative to the cost function value associated with the integrated intensity of the example dose map before any change). The same 1% change in the integrated intensity of the example dose map may be associated with a 50% change in a second cost function value. In this example, the first cost function may be regarded as non-sensitive and may be assigned or associated with a first weight, which is higher than a second weight associated with the second cost function. Of course, other metrics (that is, other than integrated intensity) to quantity the dose distribution (and changes thereof) are available.

Mathematically, the goal of the optimization procedure is to achieve the minimal cost function value. However, in radiation therapy, the inventors have come to the realization that it is the dose distribution rather than the cost function value that is a key criterion when evaluating the quality of a treatment plan. Different cost functions have different mathematical natures as to the relationship between the cost function value and the dose distribution. For some cost functions, slightly different cost function values may correspond to a significantly different dose distributions, and vice versa. The method for radiation treatment planning thereby achieves a better balance (that is, reliably handles cost functions of varying mathematical natures). Automatic assignment of weights to cost functions enables indication of how sensitive the cost function value is expected to be when changing the dose distribution (or treatment parameters that give rise to the dose distribution).

For example, for cost functions in which small changes in the cost function value would cause a very different dose distribution, a higher weight may be assigned. Such cost functions may be labelled as "non-sensitive cost functions", as their cost function values do not change as significantly as those of other cost functions. The cost function value may then be obtained with a factor of the weight. Similarly, for cost functions in which larger changes in the cost function value would cause only a slightly different dose distribution, a lower weight may be assigned. Without this case-by-case handling of cost functions, optimization procedures may not converge due to cost function value being constrained and unable to change significantly while the reference objective is not achieved.

Such non-sensitive cost functions may be determined (i.e., classified as non-sensitive) using any suitable technique. As an example, one may plot resultant dose distributions (or aspects thereof, e.g., mean values) against cost function values to establish how sensitive cost function value changes with different dose distributions. One may then assign an initial weight to the cost function based on aspects of the relationship between the resultant dose distributions and cost function values. For example, for a normal (sensitive) cost function, the initial weight may be set to 1; for a cost function considered to be moderately non-sensitive, the initial weight may be set to 100; and for a cost function considered to be very non-sensitive, the initial weight may be set to 500.

The inventors have come to the realisation that the automated handling of cost functions in view of that cost function's sensitivity routinely improves speed of optimization and accuracy of generated treatment plans. In automating the procedure, the user is not burdened with selection or handling of cost functions, the behaviour of which may vary significantly between cost functions.

Optionally, the optimization procedure comprises determining a dose distribution, where the dose distribution indicates the expected dosage in a target region of the patient, based on the reference objective. The expected dosage is the dosage that a radiotherapy system configured with treatment plan parameters (or values thereof) determined through the optimization procedure (e.g., would be expected to deliver to the target region). Examples of optimizable parameters include parameters that relate to characteristics of radiation to be delivered by the radiotherapy system, such as radiation beam angles, radiation intensity level at each angle, etc. Additionally or alternatively, the dose distribution indicates the expected dosage in a surrounding region of the patient.

Optionally, the optimization procedure may be an iterative procedure, comprising multiple optimization iterations or passes. For instance, the iterative optimization procedure may use an initial value (e.g., an initial value for radiation beam angle) to generate a sequence of improving approximate solutions for optimum parameter value (e.g., improving values for radiation beam angle), where each subsequent approximation is derived from the previous approximation. In a first optimization iteration (of the multiple optimization iterations), the optimization procedure uses the assigned initial weight value of the selected cost function when seeking to minimize the selected cost function. The selected cost function—and possibly the other cost functions of the plurality of cost functions—may be associated or mapped to an assigned weight handling parameter. During subsequent iterations of the optimization procedure, the assigned initial weight value may be modified.

In one example, for which the assigned initial weight value may be a value of 0.75, the example assigned weight handling parameter may decrease the assigned weight value by 0.05 at each subsequent iteration of the optimization procedure. Of course, the assigned weight handling parameter and associated functionality may be more complex, for instance including a threshold so as to stop assigned weight value modification after a set number of iterations, or including some polynomial-based modifying properties so as to modify the assigned weight value by a polynomial factor (e.g., $0.05 \times n^{-1}$ for n iterations).

The assigned weight handling parameter may cause the weight to increase during some or all subsequent iterations. After assigning the initial weight for each cost function, the method may increase the weight when the achieved value is worse than the reference objective. As an example, in the case of a sensitive cost function, if the achieved value is just a little bit worse (e.g., by a maximum of a predetermined value or percentage) than the reference objective, then the weight may be increased by a small amount (e.g., by 10%). If the achieved value is much worse (e.g., by a minimum of another predetermined value or percentage) than the reference objective, then the weight is increased by a big amount (e.g., by 10 times). In another example, in the case of a non-sensitive cost function, if the achieved value is just a little bit worse than the reference objective, then the weight may be increased by a small amount (e.g., by 1 time or doubled). If the achieved value is much worse than the reference objective, then the weight may be increased by a big amount (e.g., by 100 times).

Similarly, the assigned weight handling parameter may cause the weight to decrease during some or all subsequent iterations. After assigning the initial weight for each cost function, the method may decrease the weight when the achieved value is better than the reference objective. As an example, in the case of a sensitive cost function, if the achieved value is just a little bit better than the reference objective, then the weight may be decreased by a small amount (e.g., by 10%). If the achieved value is much better than the reference objective, then weight may be decreased by a big amount (e.g., by 10 times). In another example, in the case of a non-sensitive cost function, if the achieved value is just a little bit better than the reference objective, then the weight may be decreased by a small amount (e.g., by 1 time or halved). If the achieved value is much better than the reference objective, then the weight may be decreased by a big amount (e.g., 100 times).

For non-sensitive cost functions, some small change of the cost function value may cause significant differences to the dose distribution, and the inventors have realised that one has to enlarge the cost function value by changing the weight aggressively to capture this behaviour. For example, consider a scenario where a cost function value is 1 and the goal (the reference objective) is exactly achieved. For a first cost function, a cost function value of 1.1 indicates the goal is almost achieved (so—for the purposes of radiotherapy planning—it may be acceptable to have a cost function value of 1.1). However, for a second, non-sensitive, cost function, the cost function value 1.1 may indicate a significant violation of the goal. The inventors have realised that improvements are seen if one lets the optimization procedure "know" that a cost function value of 1.1 is acceptable for the first cost function, but it is not ok for the second cost function. By assigning a higher weight for the second cost function, the cost function value (i.e., the "actual" cost function value multiplied by the weight) becomes more sensitive to changes in the dose distribution.

For example, the optimization procedure seeks to decrease the cost function value. For the first cost function, 1.1 is not considered to be ideal (1 is considered to be ideal) but is considered to be acceptable. In turn, the weight may only need to be increased by a small factor (e.g., 10%), thereby illustrating that this first cost function should not "give up" after achieving 1.1 because the goal is 1. Rather, the optimization procedure may continue to work on the given first cost function by increasing the weight by a small quantity. For the second cost function, the weight may, instead, be increased more aggressively, by a much larger factor (e.g., 1000%), so that optimization procedure will, in effect, "focus" more on this second cost function. The mechanism by which the weights are increased or decreased is captured by the weight handling parameter.

Optionally, the optimization procedure may iteratively adapt the radiation treatment plan to minimize the selected cost function. That is, the optimization procedure may iteratively adapt optimizable parameters of the radiation treatment plan so as to arrive at a radiation treatment plan capable of treating a patient with clinically acceptable accuracy and expected efficacy.

The optimizable parameters may include a dose excess value, which is an amount of dosage violation that is considered acceptable. The optimizable parameters may include weights of beamlets; in a radiation beam may be divided into a number of beamlets where the contribution, at (hypothetical) unit fluence, may be determined. The weight of a beamlet is then a scaling factor, by which the unit fluence of the beamlet may be scaled to arrive at another fluence value. The optimizable parameters may include beam (or beamlet) angles, which may be the angle of a beam—relative to a reference point, such as a radiation head of a radiotherapy system, towards a target region. The optimizable parameters may include dose-volume histogram information, which provides information related to the cumulative dose per volume fraction of target or OAR. A "fraction" may be derived using a process of "fractioning," whereby a sequence of radiation therapy deliveries is provided over a predetermined period of time (e.g., 45 fractions), with each therapy delivery including a specified fraction of a total prescribed dose. The optimizable parameters may include a number of radiation beams. The optimizable parameters may include a dose per radiation beam. The optimizable parameters may include segment or control point shapes. The optimizable parameters may include segment or control point weights. The optimization procedure may adapt any or all of the optimizable parameters.

Optionally, the optimization procedure may be in respect of multiple objectives. That is, multiple objectives may be the subject of multi-objective or Pareto optimization. The method may then involve reception of a second reference objective and selection of a cost function associated with the second reference objective from the plurality of cost functions. Of course, the second reference objective may be the same as the first reference objective. For instance, the method may seek to optimize dosages involved in a treatment plan for two clinically similar target regions, in which case a same cost function may be appropriate. The second selected cost function may be associated with a second assigned weight value, where the second assigned weight value may correspond to sensitivity of the example dose distribution relative to changes in the second selected cost function. The method may then apply the optimization procedure to the radiation treatment plan for radiation treatment in the patient according to the second reference objective (as well as the first reference objective).

Optionally, the plurality of cost functions may comprise a subset of cost functions, where the subset includes at least two cost functions that share an assigned weight value. Additionally or alternatively, the at least two cost functions may share an assigned weight handling parameter. For instance, each cost function of the subset may be labelled using a flag or pointer, indicating that each cost functions are to be processed (with respect to any cost function value weight scaling or weight handling) in the same manner as one another. Of course, multiple subsets may be included, where a second subset, for example, may comprise cost functions that share some assigned weight value and/or assigned weight handling parameter. Example subset labels include "sensitive" and "non-sensitive".

Optionally, the reference objective may comprise a reference dose value for a target region of the patient. Additionally or alternatively, the reference objective may comprise a reference dose value for a surrounding region.

Optionally, the reference objective may comprise a reference volume value for a target region of the patient. Additionally or alternatively, the reference objective may comprise a reference volume value for a surrounding region.

Optionally, the cost function may be an equivalent uniform dose cost function, a dose-volume histogram cost function, or a partial volume cost function.

Optionally, the method for radiation treatment planning may include accepting user input into a graphical user interface, the user input comprising the reference objective and/or the selected cost function.

Optionally, the method for radiation treatment planning may include outputting parameter values corresponding to the treatment plan. The parameter values may comprise any or all of the following: number of beams, beam angles, a dose per beam, beamlet weights, segment or control point shapes, segment or control point weights, dose-volume histogram information, a dose excess value. In this way, the method may output parameter values (and, of course, configuration settings) for a radiotherapy system, so as to be able to deliver the radiation plan to the patient.

Embodiments of another aspect include a data processing apparatus comprising a memory storing computer-readable instructions and a processor. The processor (or controller circuitry) is configured to execute the instructions to carry out the computer-implemented method for radiation treatment planning.

Embodiments of another aspect include a computer program comprising instructions, which, when executed by computer, causes the compute to execute the computer-implemented method for radiation treatment planning.

Embodiments of another aspect include a non-transitory computer-readable storage medium comprising instructions, which, when executed by a computer, causes the compute to execute the computer-implemented method for radiation treatment planning.

The disclosed techniques, systems, or operations may be implemented in digital electronic circuitry, or in computer hardware, firmware, software, or in combinations thereof. The techniques, systems, or operations may be implemented as a computer program or a computer program product, i.e., a computer program tangibly embodied in a non-transitory information carrier, e.g., in a machine-readable storage device or in a propagated signal, for execution by, or to control the operation of, one or more hardware modules. A computer program may be in the form of a stand-alone program, a computer program portion, or more than one computer program, and may be written in any form of programming language, including compiled or interpreted languages, and it may be deployed in any form, including as a stand-alone program or as a module, component, subroutine, or other unit suitable for use in a data processing environment.

The present disclosure is described in terms of particular embodiments or examples. Other embodiments are within the scope of the following claims. For example, the steps of the present disclosure may be performed in a different order and still achieve desirable results.

BRIEF DESCRIPTION OF THE DRAWINGS

Reference is made, by way of example only, to the accompanying drawings in which.

DETAILED DESCRIPTION

Treatment planning typically involves performing an optimization procedure to optimize a number of parameters, the purpose being to provide a sufficiently high dose to the target region (or planned target volume, PTV) while reducing the dose to the surrounding healthy tissue. By balancing the different treatment-planning objectives, for example by prioritising treatment-planning objectives that relate to the dose coverage at the target region and then treatment planning that relate to sparing surrounding regions, a clinically suitable plan may be obtained. However, with conventional treatment planning methods, the user is often required to possess an advanced understanding of how the particular cost function used within optimization procedures behaves in respect of resultant dose distributions. This places an unnecessary burden on the user, which ultimately may severely slow treatment planning processes.

Figure 1:
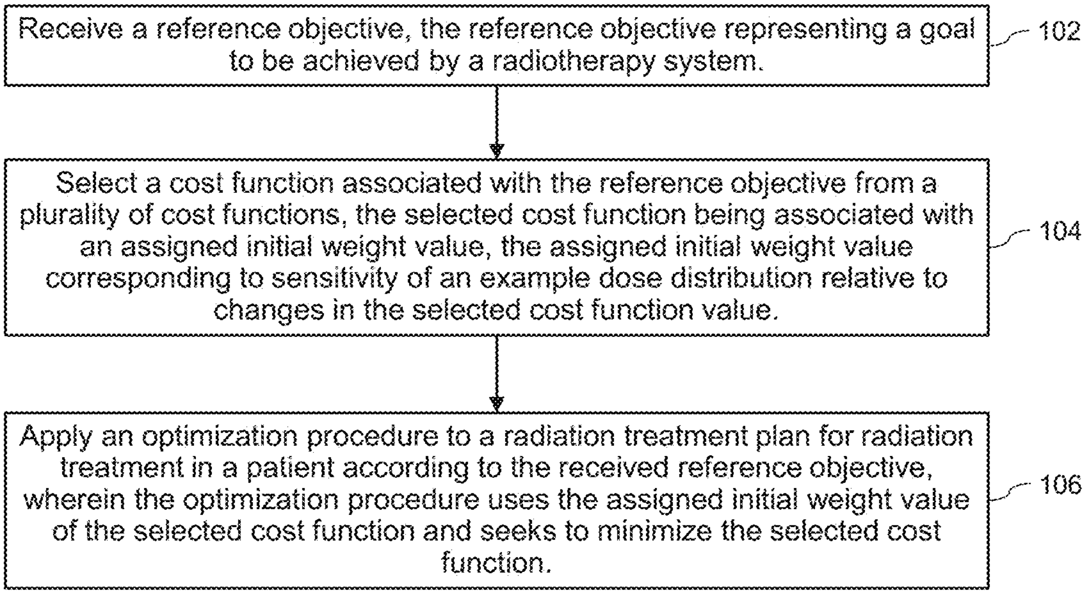
FIG. 1 is a flow chart of a general method for radiation treatment planning.

FIG. 1 shows a general method for radiation treatment planning, which addresses the burden placed on the user of having cost function expertise. At step 102, a computer receives a reference objective, which represents some goal to be achieved by a radiotherapy system (and associated radiotherapy process). At step 104, the computer selects a cost function associated with the reference objective from a plurality of cost functions. The selected cost function is associated with an assigned initial weight value, where the assigned initial weight value corresponds to the sensitivity of an example dose distribution relative to changes in the selected cost function. At step 106, the computer applies an optimization procedure to a radiation treatment plan for radiation treatment in a patient according to the received reference objective. The optimization procedure uses the assigned initial weight value of the selected cost function and seeks to minimize the selected cost function.

Any optimization procedure that accepts reference objectives, which represent some goal to be achieved by a radiotherapy system and seek to minimize a cost function (or, equivalently, maximise a reward function) is suitable for incorporation into methods according to embodiments. For instance, the method may implement the optimization procedure described in European patent application publication EP3681600A1.

Adherence to objectives and constraints involved in optimization procedures may be quantified using the cost function, where the cost function output is a measure of the difference between a dose achieved by the treatment plan (e.g., the dose in a given region) and a reference dose (e.g., a maximum acceptable dose in that region).

Figure 2A:
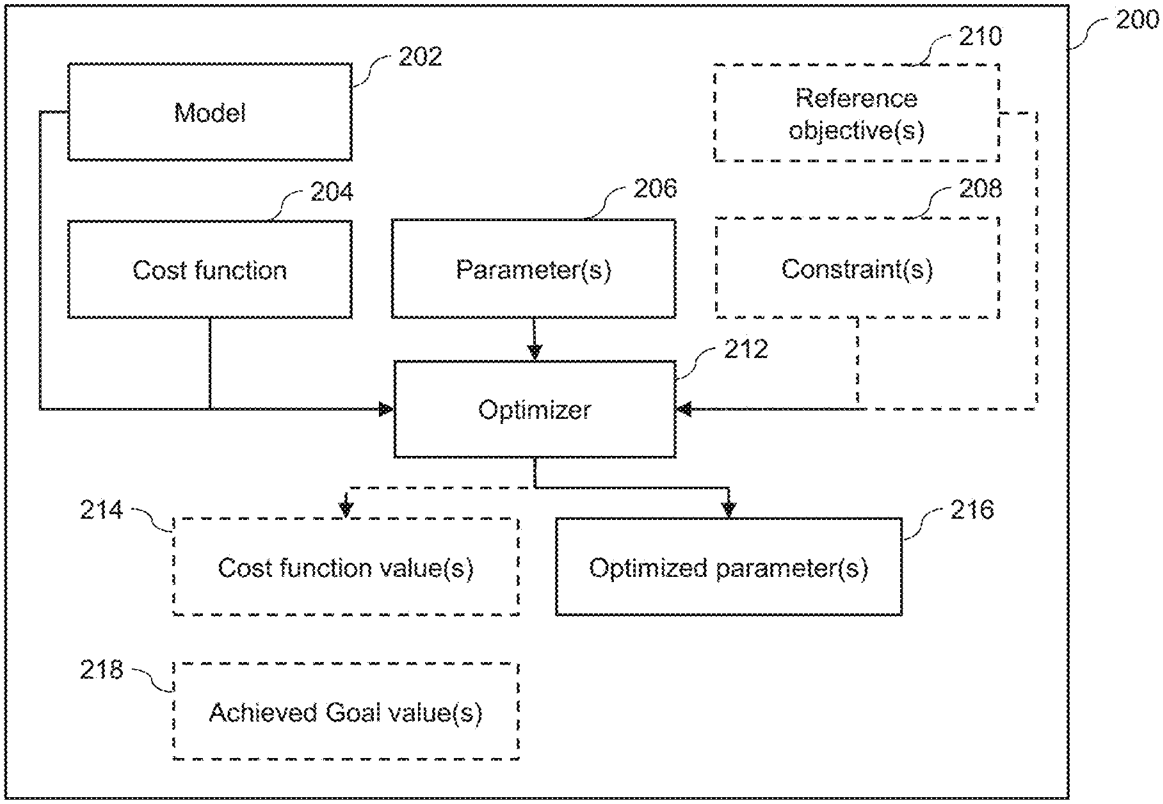
FIG. 2A is an example optimization procedure.

FIG. 2 shows a block diagram of an example optimization procedure. The optimization procedure is applicable to the optimization of a set of parameters (i.e., one or more parameters) for a radiotherapy system. The one or more parameters may be referred to as optimizable parameters, or as decision variables. Examples of optimizable parameters comprise parameters that relate to characteristics of radiation to be delivered by the radiotherapy system, such as radiation beam angles, radiation intensity level at each angle, etc. Optimization is typically carried out with respect to one or more parameters to reduce beam-on time, improve dose uniformity, etc. An example of a radiotherapy system will be described below.

The optimization module 200 may comprise an optimizer 212. Given an anatomical model 204 and one or more parameters 206, the purpose of the optimizer 212 is to provide a set of optimized parameters 216 that minimise cost function 204. The optimizer comprises at least one optimization algorithm. Examples of optimization algorithms include a simplex algorithm, a gradient-based algorithm, or an interior point algorithm, etc., or a combination thereof. Other optimization algorithms are also possible. Examples of optimization are provided in Monaco® Training Guide, Document ID: LTGMON0530 (Elekta AB).

The cost function value 214 is value of the cost function 204 when evaluated with the set of optimized parameters 216. The cost function value 214 is calculated by the optimizer 212 during optimization. The cost function value 214 may be referred to as a penalty. Optionally, the cost function value 214 is output by the optimizer 212.

The model 202 is a representation of the physical problem. The model 202 may correspond to an anatomical structure or regions thereof. The model 202 may comprise a target region (or PTV) and a surrounding region of healthy tissue or otherwise critical structures (known as organs at risk or OARs). These regions may be determined and/or defined during a process known as segmentation, performed on a two- or three-dimensional image or model of the anatomical structure. These regions may be in the form of shell structures, which are structures generated to tune the dose delivered to the tissue surrounding the target, and they may be used to control dose distribution conformality. The dose distribution may be determined by pencil beam algorithms, convolution based algorithms, and/or Monte Carlo (MC) based algorithms. Further details of how the dose may be determined are provided in Monaco® Training Guide, Document ID: LTGMON0530 (Elekta AB).

The one or more parameters 206 may be optimizable parameters (also referred to as decision variables) for which the optimizer 212 attempts to find optimum values. The one or more parameters 206 may be initialised to a predetermined value. In an example, for intensity-modulated radiation therapy, IMRT, the parameters 206 are the weight of beamlets, the parameters 206 may be initialised to a predetermined weight. The weight of a beamlet may map to an actual beamlet intensity during radiation treatment, where the intensity may be altered, for instance, by varying an aperture size or pulse time. Alternatively, the parameters 206 may be initialised to values determined in a previous step. For example, when a further optimization procedure (or pass) is performed, the parameters may be initialised to values determined in a previous optimization procedure (or pass).

The cost function 204 is a mathematical formulation that relates the parameters 206 and the model 202. The cost function 204 may be referred to as an objective function. The cost function 204 relates the dose distribution in the model 202 to a single value (the cost function value 214). For example, the cost function value 214 defines a penalty for violating objectives and/or constraints. The penalty may be evaluated by the optimizer 212 during optimization. Optionally, in constrained optimization, only objectives contribute to the cost function (that is, a constraint remains "fixed", and the optimization procedure does not permit the constraint to be violated, because. a violation of the constraint 208 simply results in a rejection of the treatment plan).

The constraints 208 comprise one or more conditions that the optimized parameters 216 must satisfy. The constraints may include hard constraints (conditions that the parameters 206 are required to satisfy). Constraints restrict the set of solutions that are obtainable. Constraints are used to define what is physically or clinically acceptable rather than what is mathematically possible. For example, for IMRT, a hard constraint may be that the weights of the beamlets must be non-negative (since a negative beamlet weight is not possible). Note that the constraint 208 is an optional feature.

The reference objective 210 comprises a goal that the optimizer 212 attempts to achieve. For example, in IMRT, the reference objective may relate to a dose-based objective and/or a volume-based objective. A dose-based objective may comprise a dose value (in Gy), for instance a maximum, minimum, or mean dose for a given region. For example, a dose-based objective may set out that dose absorbed in a 10 $mm^3$ volume should not exceed 25 Gy. A volume-based objective may comprise a relative volume (a fraction or a percentage of a volume) or an absolute volume (or, in 2-dimensional cases, an absolute area). For instance, a volume-based objective may set out that the dose absorbed in 50% of the volume of an OAR should not exceed 5 Gy. The volume (or area) may be defined in terms of physical dimensions (e.g., in $mm^2$, $cm^2$, $mm^3$, $cm^3$). Additionally, the reference objective 210 may comprise an indication of a cost function 204 to be used. Further, the reference objective 210 may comprise an indication of an anatomical structure to which the goal to be achieved is applicable. The optimizer 212 will then determine optimized parameters 216 that result in an achieved goal value 218 that is close to the reference objective 210. The reference objective may be referred to as a treatment-planning objective. Note that the reference objective 210 is an optional feature.

The reference objective 210 may therefore be an anatomy-specific function that establishes the dose and/or biological response goal. Constraints 208 are anatomy-specific functions that must be met to enable optimization convergence. When constraints are used together with objectives, constraints are always met, while objectives may not necessarily be met (instead, they are goals that the optimizer 212 tries to achieve). In the event of multiple objectives, objectives may be allocated a priority or preference, for example such that a primary objective is considered in a first optimization procedure, a secondary objective is considered in a second optimization procedure following the first optimization procedure, a tertiary objective is considered in a third optimization procedure following the second optimization procedure, and so on.

The cost function 204, together with the model 202, the parameters 206, constraints 208 (optional) and reference objective 210, may be considered to represent the optimization problem to be solved. The cost function 204, constraints 208, reference objective 210, either alone or in combination, may be referred to as a treatment-planning objective.

The optimizer 212 aims to find a set of optimized parameters 206 for which the cost function 204 is minimised. The optimized parameters 216 are an output of the optimizer 212.

Optionally, the optimizer 212 outputs the cost function value 214. The cost function value 214 is the value of the cost function 204, when evaluated with the optimized parameters 216.

Optionally, the optimizer 212 outputs an achieved goal value 218. The achieved goal value 218 is comparable to the reference objective. An achieved goal value 218 represents a value that has the same units as a given reference objective. The achieved value 218 may be different from the cost function value 214. Unlike the cost function value 214, which may be a number that is an evaluation of the cost function, the achieved value 218 may have a physical meaning. In an example, when the reference objective comprises a dosimetric objective, the achieved goal value also relates to a dose (e.g., it has the units of Gy and/or the same physical meaning as the reference objective). In an example, when the reference objective comprises a reference volume and a dose value, the achieved goal value also relates to a reference volume and a dose value (i.e., it has the same physical meaning as the reference objective). The cost function value 214 may be a number that corresponds to a cost function evaluated with a set of optimized parameters. The achieved goal value 218 would be the achieved percentage of the volume that receives the predetermined dose. In other words, achieved goal value 218 is comparable to the reference objective.

Figure 2B:
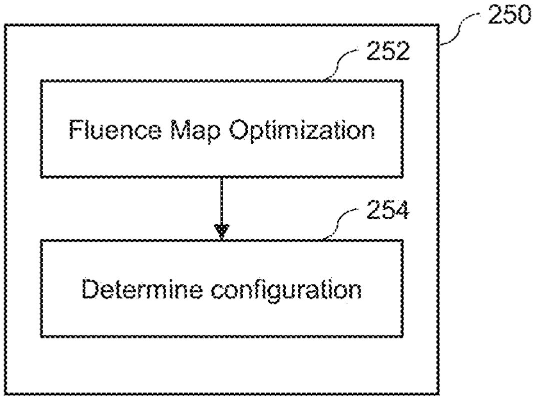
FIG. 2B is an example optimization procedure, for application in intensity-modulated radiation therapy.

FIG. 2B shows an example of a two-stage optimization procedure 250 for IMRT. Although this example applies to IMRT, it is noted that optimization procedure may be applied to other modes of radiotherapy. For instance, the optimization procedure may also be applied to volumetric modulated arc therapy, VMAT.

In IMRT, one or more radiation beams are directed to a tumour (target region). The intensity of each beam profile is non-uniform. The aim of optimization procedure 250 is to modify the intensity profile such that a high enough dose is delivered to the tumour, while reducing the dose delivered to healthy organs (surrounding region).

The method of optimization for IMRT 250 comprises two stages. The first stage 252 is fluence map optimization, FMO, and the second stage 254 is the determination of a configuration of the radiotherapy system. In FMO (stage 252), an optimal fluence map is determined. The optimal fluence map is then used to determine a configuration for the radiotherapy system in the second stage.

For FMO, each beam is divided into a number of beamlets. The contribution of each beamlet, at unit fluence, to voxels is then calculated. During optimization, the weight of each beamlet is adjusted such that a cost function is minimised. By multiplying the weight with the contribution of each beamlet at unit fluence, the full dose distribution may be obtained. The full dose distribution may be compared with any constraints and/or reference objectives to determine if the optimized solution is suitable.

Optimization comprises minimizing a cost function $f(x)$ by determining suitable values of parameters x based on certain constraints g. For FMO, the parameters x correspond to the weight of the beamlets (parameters x may also be referred to as decision variables). The output of FMO (stage 252) comprises parameters x.

The constraints g comprise restrictions. An example of a restriction is a minimum dose at voxels corresponding to a target, or a maximum dose at voxels corresponding to OAR.

In an example, a cost function $f(x)$ is:

$$f(x) = T1 + T2 + \ldots + T3, \quad \text{(Eqn. 1)}$$

where, e.g., $T1=\Sigma x_n \cdot d_n$, where, when x corresponds to weight of a beamlet, $d_n$ represents the dose that each beamlet gives to a voxel at unit intensity. $d_n$ is a non-optimizable parameter (e.g., it may depend on machine configuration and/or properties of the tissue). $d_n$ corresponds to the model 202 described above. In an example, the dose $d_n$ may be determined by pencil beam algorithms, convolution based algorithms and/or Monte Carlo (MC) based algorithms. Optionally, dose calculations use pencil beam algorithms or convolution based algorithms (which are fast but have reduced accuracy). Further details of how the dose $d_n$ may be determined are provided in Monaco® Training Guide, Document ID: LTGMON0530 (Elekta AB). The output of stage 1 may include a dose distribution.

In this example, the cost function $f(x)$ is the sum of the total dose (T1, T2, . . . , T3) where each of T1, T2, . . . , T3 represent the dose on different structures. Note that alternative formulations of the problem to be solved (e.g., by defining different cost functions or constraints) may be used.

In an example, the requirement for the dose at a target to be above a certain amount may be formulated as a constraint. Alternatively, such a requirement could be formulated as a reference objective.

Stage 252 provides a set of optimized parameters (e.g., beamlet weights x) that would provide an optimum intensity map (or fluence map). To be ready for delivery by the radiotherapy system, a further stage (stage 153) is required to translate each optimized beamlet weight into a configuration of the machine that would deliver the optimum fluence.

At stage 254, the output from stage 252 is turned into a configuration of a radiotherapy system. The configuration is useable by a radiotherapy apparatus (examples of which are described herein) for delivering radiation therapy. For example, the configuration of the radiotherapy system comprises a set of (i.e., one or more) aperture configurations. The shapes of the aperture configurations may be selected to meet the same goal as in the first stage. Aperture configurations may be realised by a beam shaping apparatus.

An aperture configuration may be referred to as a control point or a segment. The control point and/or segment comprise radiation information (e.g., energy, dose) and geometric information (segment or control point shapes) such as gantry angle and leaf position.

The shapes and weights (i.e., segment or control point weights) of the apertures (segment or control point shapes) may be determined by applying algebraic and trigonometric considerations to the arrangement of the aperture in order to implement the optimized beamlet weights of stage 252.

Alternatively, stage 254 comprises performing a second stage optimization procedure to determine an optimized aperture configuration that would implement the optimized fluence pattern determined in stage 252. The second stage optimization procedure may be referred to as aperture optimization, or aperture refinement.

Aperture optimization may comprise the following:

Receiving a set of beamlet weights (e.g., from stage 252)

Performing optimization to determine optimized aperture shapes. The optimization may be performed using an optimization procedure such as in FIG. 2B, for example. Other optimization procedures are possible.

When the beam shaping apparatus comprises a multi-leaf collimator, MLC, aperture optimization may comprise:

Receiving a set of beamlet weights from FMO and/or fluence profiles (e.g., from stage 252)

Converting the received profile into beamlet widths (the opening between a leaf pair). This results in a segment.

Optimizing the weights of the resulting segments.

Optionally, optimizing shapes of the resulting segments (using a procedure referred to as segment shape optimization).

Note that the optimization steps in stage 254 may comprise a calculation of the dose distribution. The dose distribution may be calculated using pencil beam algorithms, convolution-based algorithms and/or Monte Carlo (MC) based algorithms. Optionally, dose calculations in stage 254 use MC based algorithms (which are more accurate but computationally expensive). Further details of aperture optimization are provided in Monaco® Training Guide, Document ID: LTGMON0530 (Elekta AB).

Note that the procedure of FIG. 2B may relate to one specific angle (radiation beam angle). In an approach, a prior stage may be to determine the angles from which radiation is to be delivered. The beam angle optimization (BAO) procedure may be carried out before the procedure of FIG. 2B and the procedure of FIG. 2B may then be carried out for each determined angle.

While the example of FIG. 2B relates to a two-stage optimization procedure (FMO at stage 252 and determination of a configuration at stage 254) for IMRT, it is noted that alternative methods of optimization, such as Direct Machine Parameter Optimization (DMPO), may be used. In DMPO, the decision variable x corresponds to a parameter of a machine (e.g., an MLC leaf position) that delivers radiation.

Returning to cost function 202 in an optimization procedure, examples of cost functions include: Target EUD, Target Penalty, Quadratic Overdose, Quadratic Underdose, Serial, Parallel, Maximum Dose, Overdose DVH, Underdose DVH. The cost functions are briefly defined below. Each cost function offers different calculation methods. When the cost function comprises any of target penalty, parallel, overdose DVH, and Underdose DVH, the reference objective is a dose value and a relative volume component (e.g., a percentage) or an absolute volume (e.g., in cc).

When the cost function comprises any of Target EUD, quadratic overdose, serial, maximum dose, or conformality, the reference objective is a dose value.

Generally, the optimization procedure seeks to minimize a composite cost-function, comprised of the sum of the cost functions that may be objectives or constraints. A cost function relates an inhomogeneous dose distribution to a single value. One may use this value to define a penalty for violating an objective or constraint. The system may evaluate this penalty value during optimization procedures.

Cost functions such as serial, parallel, quadratic overdose, overdose DVH, or maximum dose aim to limit the dose at an anatomical structure (e.g., a penalty value is imposed if the dose exceeds a threshold). Cost functions such as quadratic underdose or underdose DVH aim to increase the dose at an anatomical structure. Cost functions such as Target EUD and Target Penalty aim to increase the dose at a structure. Some of the above cost functions also take a unitless number as input. The unitless number (k) may be, for example, a power law exponent.

The Target EUD cost function defines a structure as a target volume and expresses the probability that a target cell survives a given dose. This cost function requires a prescribed dose as input (i.e., the reference objective for this cost function is a dose value). The prescribed dose, in Gy, is an equivalent uniform dose (EUD). An EUD is a homogenous dose that, if delivered at an anatomical structure, has the same clinical effect that a non-homogenous dose distribution would provide.

The Target Penalty cost function takes as input a prescribed dose and a minimum volume as input (i.e., the reference objective for this cost function is a dose and a relative volume). The Target Penalty is a quadratic penalty which starts at a threshold dose. It produces steeper dose gradients after a target threshold is met. The Target Penalty is used to define the requirement that at least some fraction of the total anatomical structure volume should receive at least the target dose.

The quadratic overdose (QO) cost function is a cost function used to limit the dose in the structure to which it is applied. The QO may be applied to either targets or OARs. The QO cost function may be used to limit hot spots in a target. The QO cost function takes as input a maximum dose and a root-mean square (RMS) dose excess (i.e., the reference objectives comprise two dose values). The maximum dose defines a dose beyond which a penalty is incurred. The RMS dose excess defines the amount of violation that is acceptable.

The quadratic underdose cost function is a cost function that is applied to a target volume. The quadratic underdose function implements a quadratic penalty. The cost function takes as input a minimum dose in Gy and a dose deficit in Gy (i.e., the reference objective comprises two dose values). The minimum dose is the minimum dose allowable in a target and represents the dose under which a penalty is incurred. The dose deficit is analogous to the RMS dose excess in that it defines the amount of violation from the prescription that is acceptable.

The Serial cost function (or equivalent uniform dose cost function) is generally used with serial OARs (an example of a non-sensitive cost function, particularly when low p values are used, for instance p<3). Serial anatomical structures are those where high doses are harmful even if limited to small volumes. Examples include the spinal cord and bowel. This cost function applies large penalties for hot spots even if they are small in volume. The cost function takes as input an EUD in Gy and a power law exponent p (i.e., the reference objective comprises a dose value and a unitless number). An example mathematical formulation of a Serial EUD cost function is as follows:

$$EUD(D; V, \Delta, p, \varepsilon) := \frac{1}{|V|}\sum_{i \in V}\left(\frac{D_i}{\Delta}\right)^p \leq \varepsilon^p \quad \text{(Eqn. 2)}$$

where the cost function represents a summation of i voxels in a volume V of the patient, and where $V_i$ is a volume of an i-th voxel, $D_i$ is a dose delivered to the i-th voxel, Δ is a reference dose value, the reference dose value being a maximum radiation dose within a target region of the patient and/or a surrounding region of the patient, and ε is a constant. The inventors have come to the realisation that sensitivity of the cost function (with respect to resultant dose map) may be controlled in part using the power law exponent. For example, p<3 typically results in a non-sensitive EUD cost function (that is, the EUD cost function value does not vary significantly with significant changes in the resultant dose map, and vice versa).

The Parallel cost function (or partial volume cost function; an example of a non-sensitive cost function) is generally used for parallel OARs. Parallel structures are those where very high doses in small volumes are tolerated, if the rest of the organ is spared. Examples are lungs, parotids, kidneys, liver. The cost function takes as input a reference dose in Gy, a mean organ damage (which is a fraction of the volume of the structure that may be sacrificed), and power law exponent p (i.e., the reference objective comprises a dose value, a relative volume, and a unitless number). The cost function further takes a mean organ damage parameter in percentage form, $\zeta_{PV}$, which is the biological equivalent to the fraction of the volume of the structure in question that can be sacrificed. For instance, one may divide the function of any organ into a large number of sub-volumes (functional sub-units, tissue-repair units) that all work in parallel. The effect of radiation is assumed to knock out sub-volumes, and thereby reduce the function of the organ. Consequentially, the function is degraded on a continuous scale. Because each sub-volume has a continuous dose-response (that is, each sub-volume can lose function on a continuous scale), 50% of the organ function can be lost in two extreme ways: either by irradiating 50% of the organ volume to a dose that obliterates function, or by irradiating the entire organ to a dose that obliterates 50% of the function of each sub-volume. The total damage to the organ is therefore the mean of the functional losses of all sub-volumes. An example mathematical formulation of a partial volume, PV, parallel cost function is as follows:

$$PV(D; V, \Delta, p, \zeta) := \frac{1}{|V|}\sum_{i\in V}\frac{|V_i|\left(\frac{D_i}{\Delta}\right)^p}{1+|V_i|\left(\frac{D_i}{\Delta}\right)^p} \leq \zeta_{PV} \quad \text{(Eqn. 3)}$$

where the cost function represents a summation of i voxels in a volume V of the patient, and where $V_i$ is a volume of an i-th voxel, $D_i$ is a dose delivered to the i-th voxel, and Δ is a reference dose value, the reference dose value being a maximum radiation dose within a target region of the patient and/or a surrounding region of the patient.

The Maximum Dose, MXD, cost function is effectively a hard barrier that may be applied to target regions (structures) or surrounding regions (OAR). The Maximum Dose cost function has a penalty that takes effect whenever voxels cross a maximum dose threshold. The cost function takes as input maximum dose in Gy (i.e., the reference objective comprises a dose value). An example mathematical formulation of an MXD cost function is as follows:

$$MXD(D; V, \Delta, \alpha) = \frac{1}{|V|}\sum_{i\in V}|V_i|\,[D_i - \Delta]_+^4 \leq \alpha \quad \text{(Eqn. 4)}$$

where the cost function represents a summation of i voxels in a volume V of the patient, and where $V_i$ is a volume of an i-th voxel, $D_i$ is a dose delivered to the i-th voxel, Δ is a reference dose value, the reference dose value being a maximum radiation dose within a target region of the patient and/or a surrounding region of the patient, and α is the maximum dose threshold.

The Overdose DVH cost function (an example of a non-sensitive cost function) takes as input an objective dose in Gy and a maximum volume, $\zeta_{ODVH}$ (i.e., the reference objective comprises a dose value and a relative volume). This cost function is applied to OARs. The purpose is to keep the volume that receives more than the objective dose below the relative volume. For instance, this cost function may be used if one wants no more than 50% of a structure to receive a dose in excess of 60 Gy. An example mathematical formulation of an overdose DVH, ODVH, is as follows:

$$ODVH(D; V, \Delta, d_0) := \quad \text{(Eqn. 5)}$$

$$\begin{cases} \sum_{i\in V}|V_i|\; b_i \times b_i & \text{if } 0 < b_i \leq 1 \\ \sum_{i\in V}|V_i|\; (1 - 0.5/(b_i \times b_i)) & \text{if } b_i > 1 \leq \zeta_{OVDH} \\ 0 & \text{else} \end{cases}$$

$$\text{where, } b_i = (D_i - \Delta + d_o)/d_o$$

where the cost function represents a summation of i voxels in a volume V of the patient, and where $V_i$ is a volume of an i-th voxel, $D_i$ is a dose delivered to the i-th voxel, Δ is a reference dose value, the reference dose value being a maximum radiation dose within a target region of the patient and/or a surrounding region of the patient, and $d_o$ is a constant or a function of Δ. As an example, a hard-coded $d_0$ value of 0.04×Δ has been shown to be effective.

The Underdose DVH cost function (an example of a non-sensitive cost function) takes as input an objective dose in Gy and a minimum volume $\zeta_{UDVH}$ (i.e., the reference objective comprises a dose value and a relative volume). This cost function is applied to targets. The purpose is to keep the volume of the target that receives less than the objective dose above the minimum volume. For instance, this cost function may be used if one wants at least 80% of a structure to receive a dose of at least 60 Gy. An example mathematical formulation of an underdose DVH, UDVH, is as follows:

$$UDVH(D; V, \Delta, d_0) := \quad \text{(Eqn. 6)}$$

$$\begin{cases} \sum_{i\in V}|V_i|\; b_i \times b_i & \text{if } 0 < b_i \leq 1 \\ \sum_{i\in V}|V_i|\; (1 - 0.5/(b_i \times b_i)) & \text{if } b_i > 1 \leq 1 - \zeta_{OVDH} \\ 0 & \text{else} \end{cases}$$

$$\text{where, } b_i = (-D_i + \Delta + d_o)/d_o$$

where the cost function represents a summation of i voxels in a volume V of the patient, and where $V_i$ is a volume of an i-th voxel, $D_i$ is a dose delivered to the i-th voxel, Δ is a reference dose value, the reference dose value being a maximum radiation dose within a target region of the patient and/or a surrounding region of the patient, and $d_o$ is a constant or a function of Δ. As an example, a hard-coded $d_0$ value of 0.04×Δ has been shown to be effective.

Further details of the cost functions are provided in Monaco® Training Guide, Document ID: LTGMON0530 (Elekta AB).

The inventors have come to the realisation that the EUD cost function, the PV cost function, the ODVH cost function, and the UDVH cost function are good examples of non-sensitive cost functions. Of course, other families of cost functions may also be good candidates as non-sensitive cost functions.

Figure 3A:
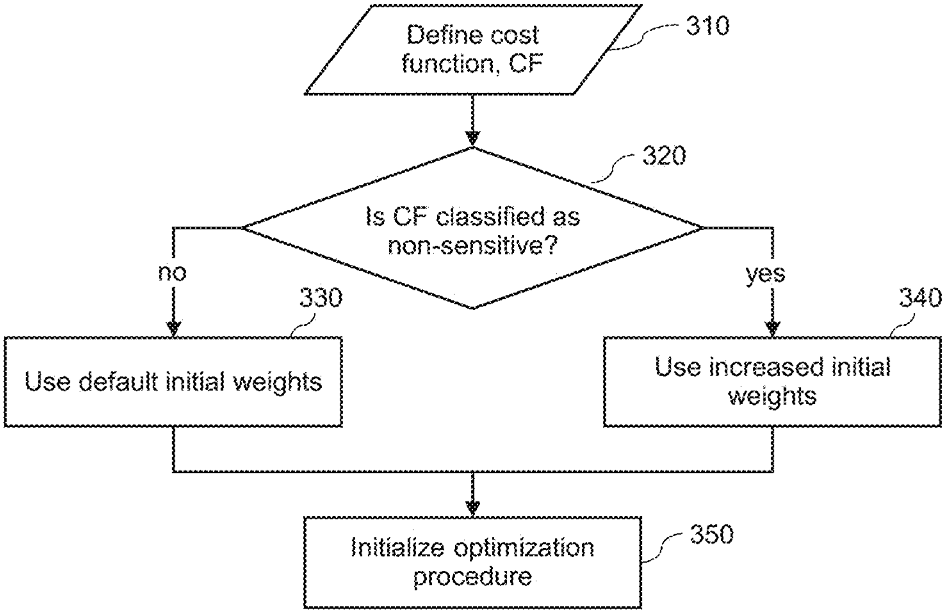
FIG. 3A is a flow chart of a method for radiation treatment planning at a first optimization iteration according to a worked example.

FIG. 3A shows a method for radiation treatment planning, involving cost function handling at the start of an optimization procedure. Consider a case of prostate cancer radiation treatment planning. The user may wish for a radiation treatment plan capable of delivering a minimum of 60 Gy to at least 80% of a tumour in the prostate region of a patient. Following input of this reference objective, the user may then select a suitable cost function (e.g., an overdose DVH cost function, as described above) at step 310.

At step 320, the computer implementing the method then determines if the selected cost function is classified as non-sensitive (i.e., the cost function value is not expected to vary significantly with significant changes in the resultant dose map, and vice versa). This classification may be performed while the method is in process, or may be predetermined—e.g., the determination at step 320 may involve use of a look-up table, to identify known cost functions, which have already been classified as non-sensitive.

Where the cost function is classified as sensitive (i.e., step 320: no), at step 330, the computer may then instruct the optimization procedure to be performed using default initial weights. Here, the default initial weight may simply be 1, in which case the cost function value is not scaled.

Where the cost function is classified as non-sensitive (i.e., step 320: yes), at step 340, the computer may then instruct the optimization procedure to be performed using increased initial weights. For example, the optimization procedure may be performed with consideration to cost function value scaled by a factor of 2. In this way, unnecessarily prolonged optimization procedures are avoided, and the optimization procedure may reach convergence more quickly.

At step 350, the computer initializes the optimization procedure using the initial weights in accordance with the selected cost function.

Figure 3B:
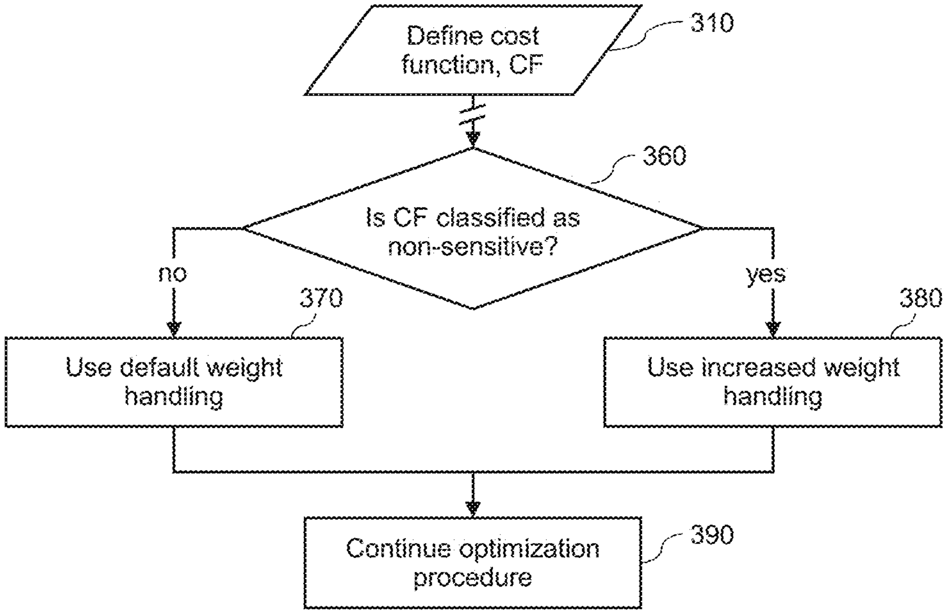
FIG. 3B is a flow chart of a method for radiation treatment planning at a subsequent optimization iteration according to a worked example.

FIG. 3B shows a method for radiation treatment planning, involving cost function handling during an iterative optimization procedure. As above, the user may then select a suitable cost function at step 310. In this example, it is assumed that the optimization procedure is ongoing (e.g., initialized in accordance with the method depicted in FIG. 3A). During a subsequent optimization iteration (that is, not the initial iteration), at step 360, the computer implementing the method then determines if the selected cost function is classified as non-sensitive.

Where the cost function is classified as sensitive (i.e., step 360: no), at step 370, the computer may then instruct the optimization procedure modify the weight values from the preceding optimization iteration using a default weight handling parameter. Here, for example, the default weight handling parameter may simply be "reduce by 0.01", in which case—and considering a weight value of 1 in the preceding optimization iteration—the weight value is reduced to 0.99 and the cost function value is scaled by 0.99.

Where the cost function is classified as non-sensitive (i.e., step 360: yes), at step 380, the computer may then instruct the optimization procedure to be performed using increased weight handling parameters. For example, the weight handling parameter associated with the non-sensitive cost function (and, for example, all non-sensitive cost functions) may be "reduce by half". Again considering a weight value of 1 in the preceding optimization iteration, the weight value is then reduced to 0.5 and the cost function value is scaled by 0.5. By imposing more aggressive weight handling, the method compensates for cost functions being non-sensitive. In this way, during optimization, the optimization procedure will automatically steer the direction by raising or lowering weights to the individual objective according to the associated cost function value sensitivity level.

At step 350, the computer continues the optimization procedure using the adjusted weights, adjusted in accordance with the weight handling parameter of the selected cost function.

Figure 4A:
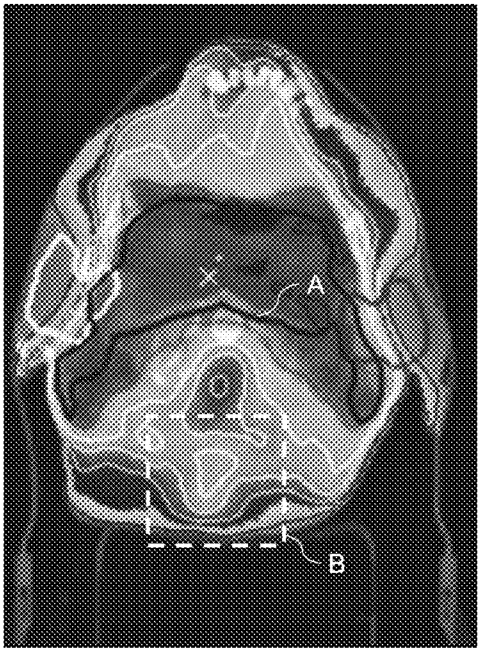
FIG. 4A is an expected dose distribution, associated with a radiation treatment plan determined according to a conventional procedure.

FIG. 4A is a dose map for a patient, overlaid on a medical image of the patient acquired using a computer tomography, CT, scan. The figure illustrates dose distribution in the form of colour-wash, where different colours represent different doses. Typically, darker colours indicate higher dose, and vice versa. If two locations have exactly same colours, then the doses in these two locations are the same. The figure includes isodose lines, where each of these connected curves displays a certain dose level. Any location at the periphery of a particular curve has the same dose. For example, one isocurve may show dose at 95% of defined dose value, and another isocurve may show dose at 80% of defined dose value.

The dose map is indicative of the expected radiation dosage in accordance with a radiation treatment plan (determined using an optimization procedure), for the treatment of tumours in the oropharynx, while seeking to minimize the dose delivered to the posterior neck. The radiation treatment plan is determined using a conventional procedure. As shown, the target region (bounding the gross and microscopic tumour as well as potentially involved lymph nodes) is the region bound with the line labelled "A". The surrounding region of concern is the area within the region bound with the dashed line labelled "B", which includes the posterior neck. A peak dose value of 49.22 Gy is delivered to the target region. In the surrounding region of concern, an undesired dose of approximately 35 Gy is expected in the central portion.

Figure 4B:
FIG. 4B is an expected dose distribution, associated with a radiation treatment plan determined according to embodiments.

FIG. 4B is a dose map for the same patient, where the associated radiation treatment plan is determined, instead, using a method according to embodiments. As shown, the expected dosage in the target region (again, bound with the line labelled "A") is largely unchanged; there is only a 4 Gy difference in the mean dose to the parotid glands in comparison to the radiation treatment plan determined using a conventional procedure. However, there is a significant decrease in the expected dosage delivered to the surrounding region (region "B").

Figure 5A:
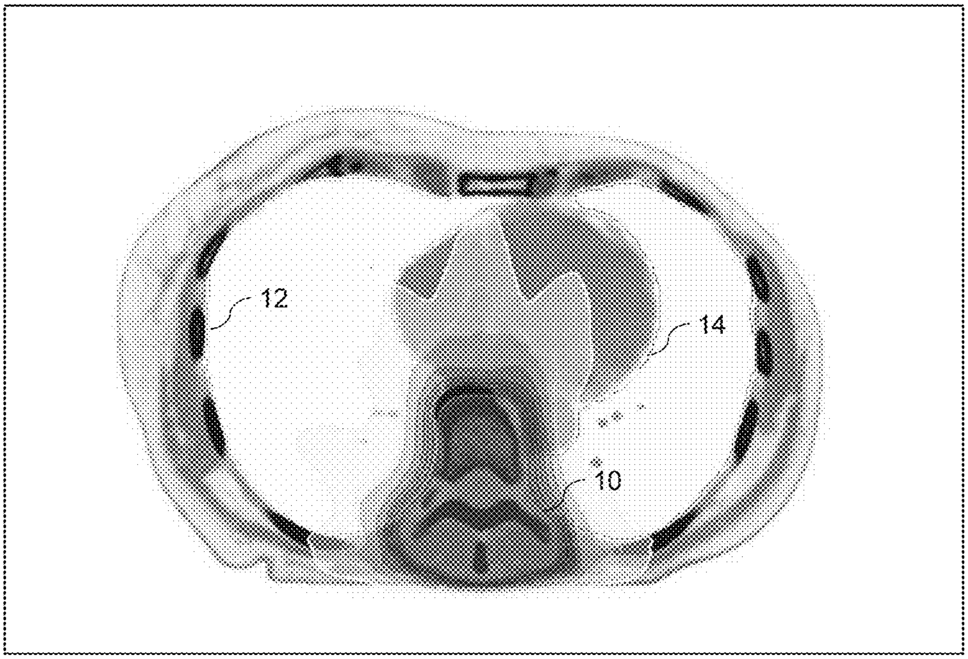
FIG. 5A is another expected dose distribution, for spinal cancer treatment, associated with a radiation treatment plan determined according to a conventional procedure.

FIG. 5A is another example dose map for a patient, overlaid on a medical image of the patient acquired using a computer tomography, CT, scan. In this example, the patient is undergoing spinal cancer treatment and the target region is therefore in the spine (the region towards the central, lower portion of the dose map). The target region is bound by curve 10. In this scan, the healthy lungs of the patient form two surrounding regions (OAR), outlined by the roughly crescent-shaped grey lines; right lung surrounding region is bound by curve 12, left lung surrounding region is bound by curve 14 (note the image is left-right inverted). An ideal treatment plan would limit dosage in the surrounding regions (lungs), while delivering an expected dosage to the target region (spine).

In this example, both left lung surrounding region and right lung surrounding region are subject to an optimization procedure in respect of a serial cost function, with p=1, and in respect of a parallel cost function, with p=2, in view of providing a maximum prescribed dose of 5 Gy. Both of these cost functions are examples of non-sensitive cost functions. This example dose map is determined using a conventional process that does not consider cost function weight value and/or weight value handling parameter.

As shown, the optimization procedure seeks to minimize the two selected cost functions are provides optimizable parameter values suitable for delivering the displayed dose map. The isodose lines (and colour-wash colours, though this aspect is lost in the greyscale rendering) radiating outwards from the target region represent expected dose levels of 90%, 80%, 70%, etc. of the reference objective (prescribed dose). As shown, in this example, there is good conformality of the dose map to the target region, though there is still a substantial spread of expected dose within both left lung surrounding region and right lung surrounding region.

Figure 5B:
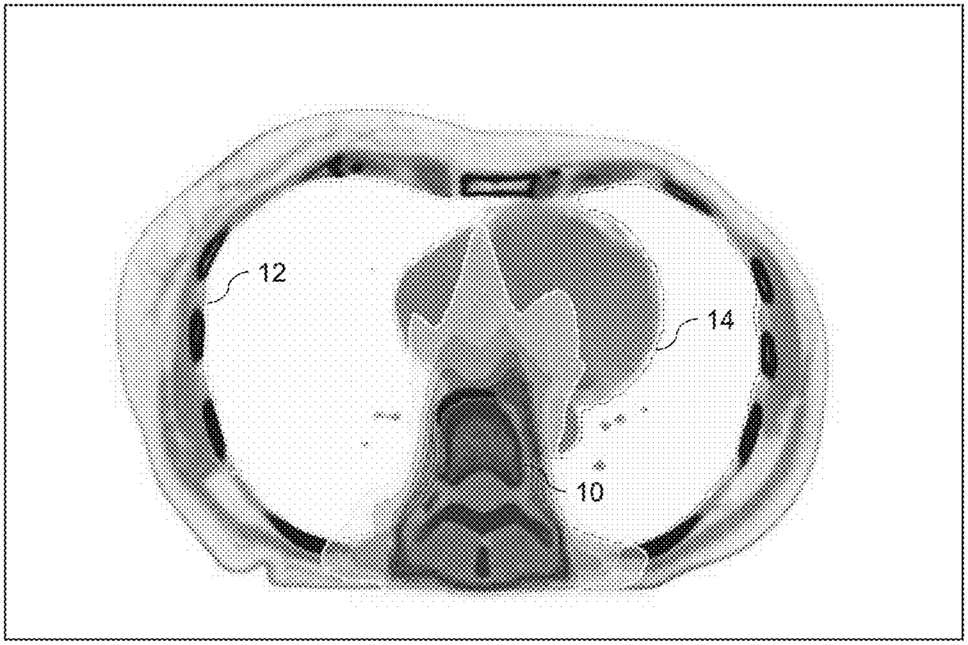
FIG. 5B is another expected dose distribution, for spinal cancer treatment, associated with a radiation treatment plan determined according to embodiments.

FIG. 5B is a dose map for the same patient, where the associated radiation treatment plan is determined, instead, using a method according to embodiments. That is, the dose map is determined using a process that does consider cost function weight value and/or weight value handling parameter. The isodose lines are equivalent both absolutely and relatively to the isodose lines shown in the dose map determined using a conventional process (that is, for instance, the 90% isodose line in FIG. 5A represents the same dose value as the 90% isodose line in FIG. 5B). As shown, with weight values and handling parameters selected in accordance with embodiments, the radiation treatment plan significantly reduces expected dose within both left lung surrounding region and right lung surrounding region relative to the treatment plan determined using a conventional process, with minimal change to the dose for the target region.

Figure 6:
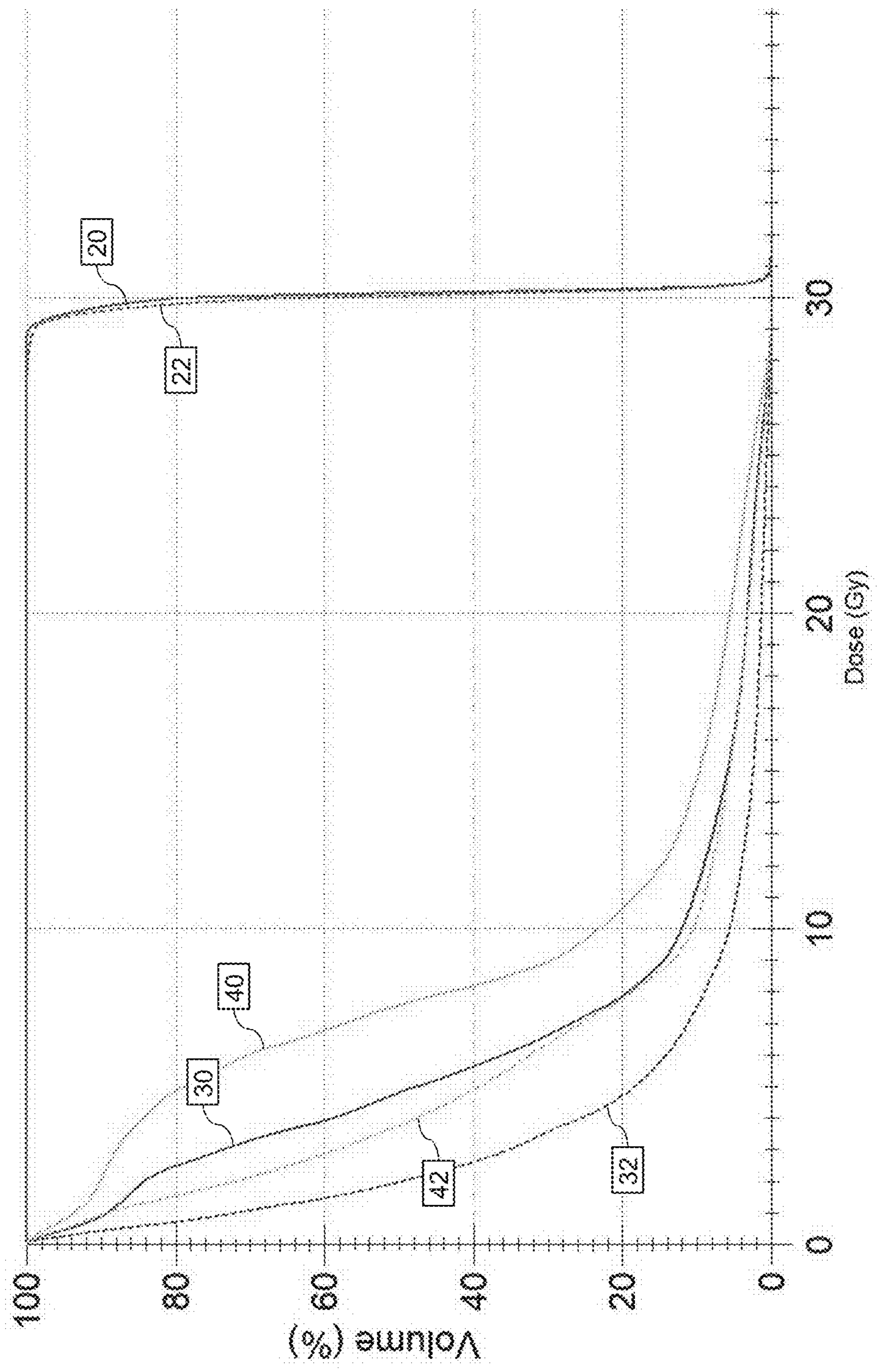
FIG. 6 is a dose-volume histogram comparing expected doses for spinal cancer treatment plans.

FIG. 6 plots the dose-volume (DVH) for the same patient and spinal cancer radiation treatment plans as shown in FIG. 5A and FIG. 5B. Solid lines (curves 20, 30, 40) correspond to the treatment plan determined without handling of weights for non-sensitive cost functions (a conventional process). Dotted lines (curves 22, 32, 42) correspond to the treatment plan determined with handling of weights for non-sensitive cost functions. Curve 20 and curve 22 are DV curves for the target region (spinal tumour). Curve 30 and curve 32 are DV curves for the left lung surrounding region. Curves 40 and 42 are DV curves for the right lung surrounding region.

As shown, the target dose-volumes are very similar for both plans, each providing roughly 30 Gy to the target region. The expected doses for both left lung and right lung associated with the conventional process without weight handling are clearly higher than the expected doses associated with a treatment plan determined using a method according to embodiments. For example, for the right lung surrounding region (curves 40, 42), without weight handling, approximately 25% of the right lung receives a dose of approximately 10 Gy. With weight handling, only approximately 10% of the right lung receives a dose of approximately 10 Gy. Accordingly, the automated handling of cost functions in view of the cost function sensitivity is shown to improve accuracy of the generated treatment plan.

Figure 7:
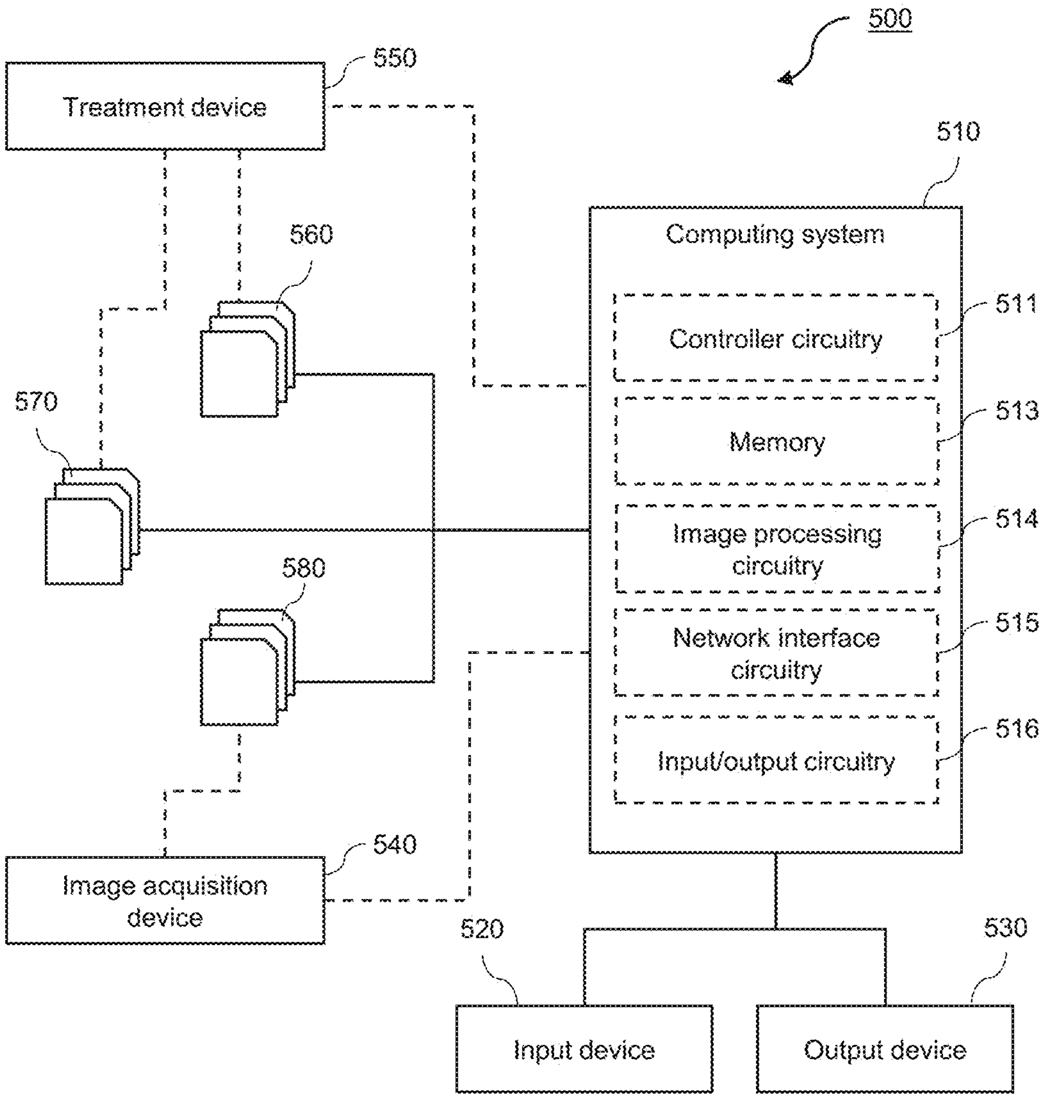
FIG. 7 is a radiotherapy system, suitable for implementing a radiation treatment plan determined according to embodiments.

FIG. 7 is a block diagram of an implementation of a radiotherapy system 500, suitable for executing methods for radiation treatment planning according to embodiments. The example radiotherapy system 500 comprises a computing system 510 within which a set of instructions, for causing the computing system 510 to perform any one or more of the methods (or steps thereof) discussed herein, may be executed. The computing system 510 may implement a treatment planning system. The computing system 510 may also be referred to as a computer. In particular, the methods described herein may be implemented by a processor or controller circuitry 511 of the treatment planning system 510.

The computing system 510 shall be taken to include any number or collection of machines, e.g., computing device(s), that individually or jointly execute a set (or multiple sets) of instructions to perform any one or more of the methods discussed herein. That is, hardware and/or software may be provided in a single computing device, or distributed across a plurality of computing devices in the computing system. In some implementations, one or more elements of the computing system may be connected (e.g., networked) to other machines, for example in a Local Area Network (LAN), an intranet, an extranet, or the Internet. One or more elements of the computing system may operate in the capacity of a server or a client machine in a client-server network environment, or as a peer machine in a peer-to-peer (or distributed) network environment. One or more elements of the computing system may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine.

The computing system 510 includes controller circuitry 511 and a memory 513 (e.g., read-only memory (ROM), flash memory, dynamic random access memory (DRAM) such as synchronous DRAM (SDRAM) or Rambus DRAM (RDRAM), etc.). The memory 513 may comprise a static memory (e.g., flash memory, static random access memory (SRAM), etc.), and/or a secondary memory (e.g., a data storage device), which communicate with each other via a bus (not shown). Controller circuitry 511 represents one or more general-purpose processors such as a microprocessor, central processing unit, accelerated processing units, or the like. More particularly, the controller circuitry 511 may comprise a complex instruction set computing (CISC) microprocessor, reduced instruction set computing (RISC) microprocessor, very long instruction word (VLIW) microprocessor, processor implementing other instruction sets, or processors implementing a combination of instruction sets. Controller circuitry 511 may also include one or more special-purpose processing devices such as an application specific integrated circuit (ASIC), a field programmable gate array (FPGA), a digital signal processor (DSP), network processor, or the like. One or more processors of the controller circuitry may have a multicore design. Controller circuitry 511 is configured to execute the processing logic for performing the operations and steps discussed herein.

The computing system 510 may further include a network interface circuitry 515. The computing system 510 may be communicatively coupled to an input device 520 and/or an output device 530, via input/output circuitry 516. In some implementations, the input device 520 and/or the output device 530 may be elements of the computing system 510. The input device 520 may include an alphanumeric input device (e.g., a keyboard or touchscreen), a cursor control device (e.g., a mouse or touchscreen), an audio device such as a microphone, and/or a haptic input device. The output device 530 may include an audio device such as a speaker, a video display unit (e.g., a liquid crystal display (LCD) or a cathode ray tube (CRT)), and/or a haptic output device. In some implementations, the input device 520 and the output device 530 may be provided as a single device, or as separate devices.

In some implementations, the computing system 510 may comprise image processing circuitry 514. Image processing circuitry 514 may be configured to process image data 580 (e.g., images, or imaging data), such as medical images obtained from one or more imaging data sources, a treatment device 550 and/or an image acquisition device 540. Image processing circuitry 514 may be configured to process, or pre-process, image data 580. For example, image processing circuitry 514 may convert received image data into a particular format, size, resolution or the like. In some implementations, image processing circuitry 514 may be combined with controller circuitry 511.

In some implementations, the radiotherapy system 500 may further comprise an image acquisition device 540 and/or a treatment device 550. The image acquisition device 540 and the treatment device 550 may be provided as a single device. In some implementations, treatment device 550 is configured to perform imaging, for example in addition to providing treatment and/or during treatment. The treatment device 550 comprises the main radiation delivery components of the radiotherapy system.

Image acquisition device 540 may be configured to perform positron emission tomography (PET), computed tomography (CT), magnetic resonance imaging (MRI), single positron emission computed tomography (SPECT), X-ray, and the like.

Image acquisition device 540 may be configured to output image data 580, which may be accessed by computing system 510. Treatment device 550 may be configured to output treatment data 560, which may be accessed by computing system 510.

Computing system 510 may be configured to access or obtain treatment data 560, planning data 570 and/or image data 580. Treatment data 560 may be obtained from an internal data source (e.g., from memory 513) or from an external data source, such as treatment device 550 or an external database. Planning data 570 may be obtained from memory 513 and/or from an external source, such as a planning database. Planning data 570 may comprise information obtained from one or more of the image acquisition device 540 and the treatment device 550.

The various methods described above may be implemented by a computer program. The computer program may include computer code (e.g., instructions) arranged to instruct a computer to perform the functions of one or more of the various methods described above. For example, the steps of the methods described in relation to FIG. 1, FIG. 2, and/or FIG. 3 may be performed by the computer code. The steps of the methods described above may be performed in any suitable order. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD. The instructions may also reside, completely or at least partially, within the memory 513 and/or within the controller circuitry 511 during execution thereof by the computing system 510, the memory 513 and the controller circuitry 511 also constituting computer-readable storage media.

In an implementation, the modules, components and other features described herein may be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may comprise a special-purpose processor, such as an FPGA or an ASIC. A hardware component may also include programmable logic or circuitry that is temporarily configured by software to perform certain operations.

In addition, the modules and components may be implemented as firmware or functional circuitry within hardware devices. Further, the modules and components may be implemented in any combination of hardware devices and software components, or only in software (e.g., code stored or otherwise embodied in a machine-readable medium or in a transmission medium).

Figure 8:
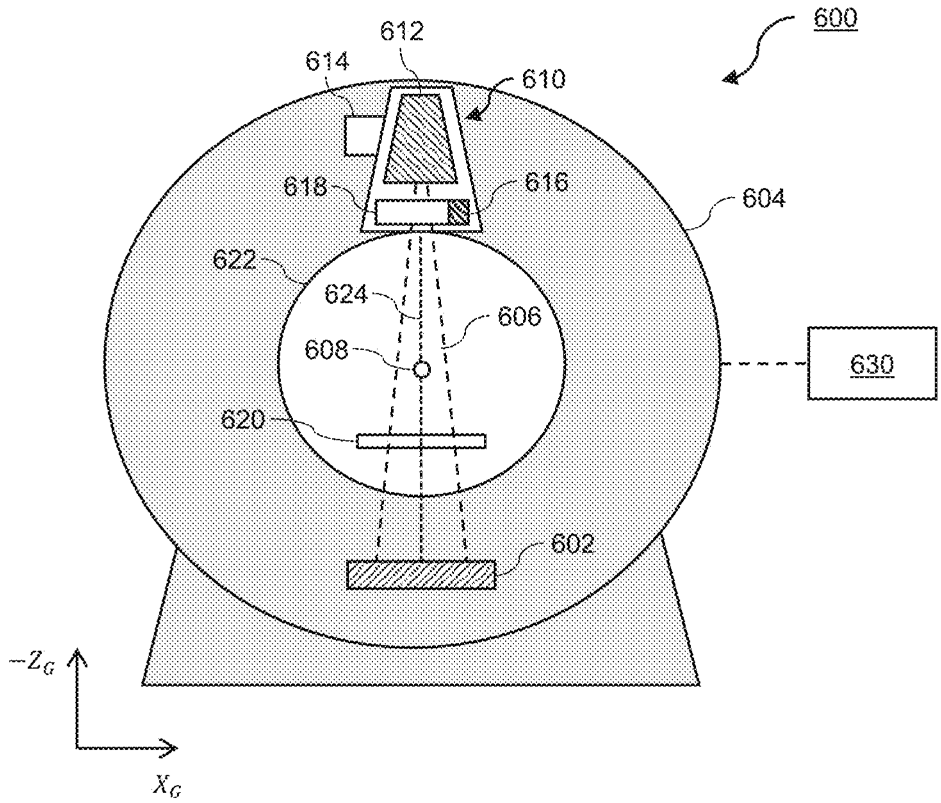
FIG. 8 is a radiotherapy device or apparatus, suitable for implementing a radiation treatment plan determined according to embodiments.

FIG. 8 depicts a radiotherapy apparatus, suitable for implementing radiation treatment plans determined according to embodiments. The cross-section through radiotherapy apparatus 600 includes a radiation head 610 and a beam receiving apparatus 602, both of which are attached to a gantry 604. The radiation head 610 includes a radiation source 612, which emits a beam of radiation 606. The radiation head 610 also includes a beam shaping apparatus 618, which controls the size and shape of the radiation field associated with the beam.

The beam receiving apparatus 602 is configured to receive radiation emitted from the radiation head 610, for the purpose of absorbing and/or measuring the beam of radiation. In the view shown, the radiation head 610 and the beam receiving apparatus 602 are positioned diametrically opposed to one another.

The gantry 604 is rotatable, and supports the radiation head 610 and the beam receiving apparatus 602 such that they are rotatable around an axis of rotation 608, which may coincide with the patient longitudinal axis. The gantry provides rotation of the radiation head 610 and the beam receiving apparatus 602 in a plane perpendicular to the patient longitudinal axis (e.g., a sagittal plane). Three gantry directions $X_G$, $Y_G$, $Z_G$ may be defined, where the $Y_G$ direction is perpendicular with gantry axis of rotation. The $Z_G$ direction extends from a point on the gantry corresponding to the radiation head, towards the axis of rotation of the gantry. Therefore, from the patient frame of reference, the $Z_G$ direction rotates around as the gantry rotates.

Radiotherapy apparatus 600 also includes a support surface 620 on which a subject (or patient) is supported during radiotherapy treatment. The radiation head 610 is configured to rotate around the axis of rotation 608 such that the radiation head 610 directs radiation towards the subject from various angles around the subject in order to spread out the radiation dose received by healthy tissue to a larger region of healthy tissue while building up a prescribed dose of radiation at a target region.

The radiotherapy apparatus 600 is configured to deliver a radiation beam towards a radiation isocentre, which is substantially located on the axis of rotation 608 at the centre of the gantry 604 regardless of the angle at which the radiation head 610 is placed.

The rotatable gantry 604 and radiation head 610 are dimensioned so as to allow a central bore 622 to exist. The central bore 622 provides an opening, sufficient to allow a subject to be positioned therethrough without the possibility of being incidentally contacted by the radiation head 610 or other mechanical components as the gantry rotates the radiation head 610 about the subject.

The radiation head 610 emits the radiation beam 606 along a beam axis 624 (or radiation axis or beam path), where the beam axis 624 is used to define the direction in which the radiation is emitted by the radiation head. The radiation beam 606 is incident on the beam receiving apparatus 602, which may include at least one of a beam stopper and a radiation detector. The beam receiving apparatus 602 is attached to the gantry 604 on a diametrically opposite side to the radiation head 610 to attenuate and/or detect a beam of radiation after the beam has passed through the subject.

The radiation beam axis 624 may be defined as, for example, a centre of the radiation beam 606 or a point of maximum intensity.

The beam shaping apparatus 618 delimits the spread of the radiation beam 606. The beam shaping apparatus 618 is configured to adjust the shape and/or size of a field of radiation produced by the radiation source. The beam shaping apparatus 618 does this by defining an aperture (also referred to as a window or an opening) of variable shape to collimate the radiation beam 606 to a chosen cross-sectional shape. In this example, the beam shaping apparatus 618 may be provided by a combination of a diaphragm and an MLC. Beam shaping apparatus 618 may also be referred to as a beam modifier.

The radiotherapy apparatus 600 may be configured to deliver both coplanar and non-coplanar (also referred to as tilted) modes of radiotherapy treatment. In coplanar treatment, radiation is emitted in a plane which is perpendicular to the axis of rotation of the radiation head 610. In non-coplanar treatment, radiation is emitted at an angle which is not perpendicular to the axis of rotation. In order to deliver coplanar and non-coplanar treatment, the radiation head 610 may move between at least two positions, one in which the radiation is emitted in a plane which is perpendicular to the axis of rotation (coplanar configuration) and one in which radiation is emitted in a plane which is not perpendicular to the axis of rotation (non-coplanar configuration).

In the coplanar configuration, the radiation head is positioned to rotate about a rotation axis and in a first plane. In the non-coplanar configuration, the radiation head is tilted with respect to the first plane such that a field of radiation produced by the radiation head is directed at an oblique angle relative to the first plane and the rotation axis. In the non-coplanar configuration, the radiation head is positioned to rotate in a respective second plane parallel to and displaced from the first plane. The radiation beam is emitted at an oblique angle with respect to the second plane, and therefore as the radiation head rotates the beam sweeps out a cone shape.

The beam receiving apparatus 602 remains in the same place relative to the rotatable gantry when the radiotherapy apparatus is in both the coplanar and non-coplanar modes. Therefore, the beam receiving apparatus 602 is configured to rotate about the rotation axis in the same plane in both coplanar and non-coplanar modes. This may be the same plane as the plane in which the radiation head rotates.

The beam shaping apparatus 610 is configured to reduce the spread of the field of radiation in the non-coplanar configuration in comparison to the coplanar configuration.

The radiotherapy apparatus 600 includes a controller 630, which is programmed to control the radiation source 612, beam receiving apparatus 806 and the gantry 802. Controller 840 may perform functions or operations such as treatment planning, treatment execution, image acquisition, image processing, motion tracking, motion management, and/or other tasks involved in a radiotherapy process.

Controller 630 is programmed to control features of apparatus 600 according to a radiotherapy treatment plan for irradiating a target region, also referred to as a target tissue, of a patient. The treatment plan includes information about a particular dose to be applied to a target tissue, as well as other parameters such as beam angles, dose-histogram-volume information, the number of radiation beams to be used during therapy, the dose per beam, and the like. Controller 630 is programmed to control various components of apparatus 600, such as gantry 604, radiation head 610, beam receiving apparatus 602, and support surface 620, according to the treatment plan. The treatment plan may be determined using methods according to embodiments.

Hardware components of controller 630 may include one or more computers (e.g., general purpose computers, workstations, servers, terminals, portable/mobile devices, etc.); processors (e.g., central processing units (CPUs), graphics processing units (GPUs), microprocessors, digital signal processors (DSPs), field programmable gate arrays (FPGAs), special-purpose or specially-designed processors, etc.); memory/storage devices such as a memory (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. Software components of controller 630 may include operation device software, application software, etc.

The radiation head 610 may be connected to a head actuator 614, which is configured to actuate the radiation head 610, for example between a coplanar configuration and one or more non-coplanar configurations. This may involve translation and rotation of the radiation head 610 relative to the gantry. In some implementations, the head actuator may include a curved rail along which the radiation head 610 may be moved to adjust the position and angle of the radiation head 610. The controller 630 may control the configuration of the radiation head 630 via the head actuator 614.

The beam shaping apparatus 618 includes a shaping actuator 616. The shaping actuator is configured to control the position of one or more elements in the beam shaping apparatus 618 in order to shape the radiation beam 606. In some implementations, the beam shaping apparatus 618 includes an MLC, and the shaping actuator 616 includes means for actuating leaves of the MLC. The beam shaping apparatus 618 may further comprise a diaphragm, and the shaping actuator 616 may include means for actuating blocks of the diaphragm. The controller 630 may control the beam shaping apparatus 618 via the shaping actuator 616.

A treatment plan may comprise positioning information of beam shaping apparatus 618. The positioning information of beam shaping apparatus 618 may comprise information indicating a configuration of one or more elements of beam shaping apparatus 618, such as leaf configuration of an MLC of beam shaping apparatus 618, a configuration of a diaphragm of beam shaping apparatus 618, a configuration of an opening (e.g., window or aperture) of the MLC, and/or the like.

As described herein, the purpose of an optimizer (or of an optimization procedure) is to find a set of optimized parameters for which a cost function is minimised. However, it will be understood that, alternatively and equivalently, the purpose of the optimizer (or of the optimization procedure) may be taken to be to find a set of optimized parameters for which a reward function is maximised.

Unless specifically stated otherwise, as apparent from the following discussion, it is appreciated that throughout the description, discussions utilizing terms such as “receiving”, “determining”, “comparing”, “enabling”, “maintaining,” “identifying,”, “obtaining”, “accessing” or the like, refer to the actions and processes of a computer system, or similar electronic computing device, that manipulates and transforms data represented as physical (electronic) quantities within the computer system’s registers and memories into other data similarly represented as physical quantities within the computer system memories or registers or other such information storage, transmission or display devices.

While certain embodiments have been described, these embodiments have been presented by way of example only, and are not intended to limit the scope of the present disclosure. Indeed, the novel methods and apparatuses described herein may be embodied in a variety of other forms; furthermore, various omissions, substitutions and changes in the form of methods and apparatus described herein may be made.

The following statements may be useful for understanding the present disclosure:

Statement 1: a computer-implemented method for radiation treatment planning, the method comprising: receiving a reference objective, the reference objective representing a goal to be achieved by a radiotherapy system; selecting a cost function associated with the reference objective from a plurality of cost functions, the selected cost function being associated with an assigned initial weight value, the assigned initial weight value corresponding to sensitivity of an example dose distribution relative to changes in the selected cost function; applying an optimization procedure to a radiation treatment plan for radiation treatment in a patient according to the received reference objective, wherein the optimization procedure uses the assigned initial weight value of the selected cost function and seeks to minimize the selected cost function.

Statement 2: the method of statement 1, wherein the optimization procedure comprises determining a dose distribution indicating expected dosage in a target region of the patient and/or a surrounding region of the patient, based on the reference objective.

Statement 3: the method of statement 1 or statement 2, wherein the selected cost function is associated with an assigned weight handling parameter, and the optimization procedure comprises multiple optimization passes, wherein: a first optimization pass uses the assigned initial weight value of the selected cost function and seeks to minimize the selected cost function; and subsequent optimization passes use the assigned weight handling parameter of the selected cost function to modify the assigned initial weight value.

Statement 4: the method of any preceding statement, wherein the optimization procedure iteratively adapts the radiation treatment plan to minimize the selected cost function.

Statement 5: the method of any preceding statement, wherein the optimization procedure seeks to minimize the selected cost function with respect to one or more optimizable parameters.

Statement 6: the method of statement 5, wherein the one or more optimizable parameters comprise one or more of: a dose excess value, beamlets weights, beam angles, dose-histogram-volume information, a number of radiation beams, and a dose per beam.

Statement 7: the method of any preceding statement, further comprising: receiving a second reference objective; selecting a cost function associated with the second reference objective from the plurality of cost functions, the second selected cost function being associated with a second assigned weight value, the second assigned weight value corresponding to sensitivity of the example dose distribution relative to changes in the second selected cost function; and applying the optimization procedure to the radiation treatment plan for radiation treatment in the patient according to the second reference objective.

Statement 8: the method of any preceding statement, wherein the plurality of cost functions comprises a subset of cost functions, the subset comprising at least two cost functions that share an assigned weight value and/or an assigned weight handling parameter.

Statement 9: the method of any preceding statement, wherein the reference objective comprises a reference dose value for a target region of the patient and/or a surrounding region.

Statement 10: the method of any preceding claim, wherein the reference objective comprises a reference volume value for a target region of the patient and/or a surrounding region.

Statement 11: the method of any preceding statement, wherein the plurality of cost functions comprises any or all of the following: an equivalent uniform dose cost function, proportional to: $\Sigma_{i\in V}|V_i|(D_i/\Delta)^p$; a partial volume cost function, proportional to:

$$\sum\nolimits_{i\in V}\frac{|V_i|(D_i/\Delta)^p}{1+|V_i|(D_i/\Delta)^p};$$

and a dose-volume histogram cost function, proportional to:

$$\begin{cases}\sum\nolimits_{i\in V}|V_i|\ b_i\times b_i & \text{if } 0<b_i\le 1\\ \sum\nolimits_{i\in V}|V_i|\ (1-0.5/(b_i\times b_i)) & \text{if } b_i>1\\ 0 & \text{else}\end{cases},$$

where $b_i=(\pm D_i\mp\Delta+d_o)/d_o$, and wherein the cost function represents a summation of i voxels in a volume V of the patient, and wherein $V_i$ is a volume of an i-th voxel, $D_i$ is a dose delivered to the i-th voxel, $\Delta$ is a reference dose value, the reference dose value being a maximum radiation dose within a target region of the patient and/or a surrounding region of the patient, p is a power law exponent, and $d_0$ is a constant or a function of $\Delta$.

Statement 12: the method of any preceding statement, further comprising accepting user input into a graphical user interface, the user input comprising the reference objective and/or the selected cost function.

Statement 13: the method of any preceding statement, further comprising: determining parameter values corresponding to the radiation treatment plan, wherein the parameter values comprise one or more of: a dose excess value, beamlet weights, beam angles, dose-histogram-volume information, a number of radiation beams, and a dose per beam; and outputting the parameter values.

Statement 14: a data processing apparatus comprising: a memory storing computer-executable instructions; and a processor configured to execute the instructions to carry out the method of any of statements 1 to 13.

Statement 15: a computer program comprising instructions which, when the program is executed by a computer, cause the computer to carry out the method of any of statements 1 to 13.

Statement 16: a non-transitory computer-readable storage medium comprising instructions which, when executed by a computer, cause the computer to carry out the method of any of statements 1 to 13.

What is claimed is:

1. A computer-implemented method for radiation treatment planning, the method comprising:

receiving a reference objective, the reference objective representing a goal to be achieved by a radiotherapy system;

selecting a cost function associated with the reference objective from a plurality of cost functions, the selected cost function being associated with an assigned initial weight value, the assigned initial weight value corresponding to sensitivity of an example dose distribution relative to one or more changes in an output of the selected cost function; and applying an optimization procedure to a radiation treatment plan for radiation treatment in a patient according to the received reference objective, wherein the optimization procedure uses the assigned initial weight value of the selected cost function and seeks to minimize the selected cost function.

2. The method of claim 1, wherein the optimization procedure comprises determining a dose distribution indicating expected dosage in a target region of the patient and/or a surrounding region of the patient, based on the reference objective.

3. The method of claim 1, wherein the selected cost function is associated with an assigned weight handling parameter, and the optimization procedure comprises multiple optimization iterations, wherein:

a first optimization iteration uses the assigned initial weight value of the selected cost function and seeks to minimize the selected cost function; and subsequent optimization iterations use the assigned weight handling parameter of the selected cost function to modify the assigned initial weight value.

4. The method of claim 1, wherein the optimization procedure iteratively adapts the radiation treatment plan to minimize the selected cost function.

5. The method of claim 1, wherein the optimization procedure seeks to minimize the selected cost function with respect to one or more optimizable parameters.

6. The method of claim 5, wherein the one or more optimizable parameters comprise one or more of: number of beams, beam angles, a dose per beam, beamlet weights, segment or control point shapes, segment or control point weights, dose-volume histogram information, a dose excess value.

7. The method of claim 1, further comprising:

receiving a second reference objective;

selecting a cost function associated with the second reference objective from the plurality of cost functions, the second selected cost function being associated with a second assigned weight value, the second assigned weight value corresponding to sensitivity of the example dose distribution relative to changes in the second selected cost function; and applying the optimization procedure to the radiation treatment plan for radiation treatment in the patient according to the second reference objective.

8. The method of claim 1, wherein the plurality of cost functions comprises a subset of cost functions, the subset comprising at least two cost functions that share an assigned weight value and/or an assigned weight handling parameter.

9. The method of claim 1, wherein the reference objective comprises a reference dose value for a target region of the patient and/or a surrounding region.

10. The method of claim 1, wherein the reference objective comprises a reference volume value for a target region of the patient and/or a surrounding region.

11. The method of claim 1, wherein the plurality of cost functions comprises any or all of the following:

an equivalent uniform dose cost function, proportional to:

$$\sum_{i\in V}|V_i|(D_i/\Delta)^p;$$

a partial volume cost function, proportional to:

$$\sum_{i\in V}\frac{|V_i|(D_i/\Delta)^p}{1+|V_i|(D_i/\Delta)^p};$$

and a dose-volume histogram cost function, proportional to:

$$\begin{cases}\sum_{i\in V}|V_i|\ b_i\times b_i & \text{if } 0<b_i\le 1\\ \sum_{i\in V}|V_i|\ (1-0.5/(b_i\times b_i)) & \text{if } b_i>1\\ 0 & \text{else}\end{cases},$$

wherein $b_i=(\pm D_i\Delta+d_o)/d_o$, and wherein the cost function represents a summation of i voxels in a volume V of the patient, wherein $V_i$ is a volume of an i-th voxel, $D_i$ is a dose delivered to the i-th voxel, Δ is a reference dose value, and wherein the reference dose value corresponds to or includes a maximum radiation dose within a target region of the patient and/or a surrounding region of the patient, p is a power law exponent, and $d_0$ is a constant or a function of Δ.

12. The method of claim 1, further comprising accepting user input into a graphical user interface, the user input comprising the reference objective and/or the selected cost function.

13. The method of claim 1, further comprising:

determining parameter values corresponding to the radiation treatment plan, wherein the parameter values comprise one or more of:

number of beams, beam angles, a dose per beam, beamlet weights, segment or control point shapes, segment or control point weights, dose-volume histogram information, a dose excess value; and outputting the parameter values.

14. A data processing apparatus comprising:

a memory storing computer-executable instructions; and a processor configured to execute the instructions to:

receive a reference objective, the reference objective representing a goal to be achieved by a radiotherapy system;

select a cost function associated with the reference objective from a plurality of cost functions, the selected cost function being associated with an assigned initial weight value, the assigned initial weight value corresponding to sensitivity of an example dose distribution relative to one or more changes in an output of the selected cost function value; and apply an optimization procedure to a radiation treatment plan for radiation treatment in a patient according to the received reference objective, wherein the optimization procedure uses the assigned initial weight value of the selected cost function and seeks to minimize the selected cost function.

15. A computer program comprising instructions which, when the program is executed by a computer, cause the computer to:

receive a reference objective, the reference objective representing a goal to be achieved by a radiotherapy system;

select a cost function associated with the reference objective from a plurality of cost functions, the selected cost function being associated with an assigned initial weight value, the assigned initial weight value corresponding to sensitivity of an example dose distribution relative to one or more changes in an output of the selected cost function value; and apply an optimization procedure to a radiation treatment plan for radiation treatment in a patient according to the received reference objective, wherein the optimization procedure uses the assigned initial weight value of the selected cost function and seeks to minimize the selected cost function.

16. A non-transitory computer-readable storage medium comprising instructions which, when executed by a computer, cause the computer to:

receive a reference objective, the reference objective representing a goal to be achieved by a radiotherapy system;

select a cost function associated with the reference objective from a plurality of cost functions, the selected cost function being associated with an assigned initial weight value, the assigned initial weight value corresponding to sensitivity of an example dose distribution relative to one or more changes in an output of the selected cost function value; and apply an optimization procedure to a radiation treatment plan for radiation treatment in a patient according to the received reference objective, wherein the optimization procedure uses the assigned initial weight value of the selected cost function and seeks to minimize the selected cost function.

* * * * *